(12) United States Patent
Feng et al.

(10) Patent No.: US 12,089,917 B2
(45) Date of Patent: Sep. 17, 2024

(54) NEAR-INFRARED SPECTROSCOPY TOMOGRAPHY RECONSTRUCTION METHOD BASED ON NEURAL NETWORK

(71) Applicant: BEIJING UNIVERSITY OF TECHNOLOGY, Beijing (CN)

(72) Inventors: Jinchao Feng, Beijing (CN); Kebin Jia, Beijing (CN); Qiuwan Sun, Beijing (CN); Zhe Li, Beijing (CN); Zhonghua Sun, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 520 days.

(21) Appl. No.: 16/620,860

(22) PCT Filed: Dec. 21, 2018

(86) PCT No.: PCT/CN2018/122661
§ 371 (c)(1),
(2) Date: Dec. 9, 2019

(87) PCT Pub. No.: WO2019/200959
PCT Pub. Date: Oct. 24, 2019

(65) Prior Publication Data
US 2020/0196870 A1 Jun. 25, 2020

(30) Foreign Application Priority Data

Apr. 16, 2018 (CN) .......................... 201810338705.2

(51) Int. Cl.
*A61B 5/00* (2006.01)
*G06N 3/084* (2023.01)
(Continued)

(52) U.S. Cl.
CPC .......... *A61B 5/0073* (2013.01); *A61B 5/0075* (2013.01); *G06N 3/084* (2013.01);
(Continued)

(58) Field of Classification Search
None
See application file for complete search history.

(56) References Cited

U.S. PATENT DOCUMENTS

| 11,371,934 B2 * | 6/2022 | Han ........................ G01N 33/66 |
| 2016/0097716 A1 * | 4/2016 | Gulati .................. A61B 5/1495 |
| | | 250/340 |

(Continued)

FOREIGN PATENT DOCUMENTS

| CN | 101342075 A | 1/2009 |
| CN | 105534606 A | 5/2016 |

(Continued)

OTHER PUBLICATIONS

Li, Ting, "Research on the Fast Reconstruction of OT Based on the Parallel BP Neural Network and Foundation Research on the in vivo Monitoring of Thermal Coagulation of Biological Tissue" Thesis Paper of Nanjing University of Aeronautics and Astronautics the Graduate School College of Automatization; (Dec. 2008) ; English Abstract is at p. 5.

(Continued)

*Primary Examiner* — Soo Shin
(74) *Attorney, Agent, or Firm* — J.C. PATENTS

(57) ABSTRACT

The present disclosure disclose a near-infrared spectroscopy tomography reconstruction method based on neural network which belongs to the field of medical image processing. In the Boltzmann radiation transmission equation, transmission process of light is regarded as absorption and scattering process of photons in medium, and interaction between light and tissue is determined by absorption coefficient, scattering coefficient and phase function of the response scattering distribution. In the transmission, only the particle property of light is taken into account, not the fluctuation of light. Therefore, polarization and interference phenomena related to the fluctuation of light are not considered, and only the (Continued)

energy transmission of light is tracked. The reconstruction method based on BP neural network is used to reconstruct the distribution of optical absorption coefficient, reconstruction results of absorption coefficient distribution can be obtained by calculation. This method can not only reconstruct the absorption coefficient distribution accurately, but also has high computational efficiency.

2 Claims, 5 Drawing Sheets

(51) Int. Cl.
    *G06N 5/046*     (2023.01)
    *G06N 20/00*     (2019.01)
    *G06T 11/00*     (2006.01)

(52) U.S. Cl.
    CPC ............ *G06N 5/046* (2013.01); *G06N 20/00* (2019.01); *G06T 11/006* (2013.01); *G06T 2210/41* (2013.01)

(56) References Cited

U.S. PATENT DOCUMENTS

2022/0018762 A1\* 1/2022 Ekin .................... A61B 5/1451
2022/0192524 A1\* 6/2022 Leabman ............. A61B 5/7225

FOREIGN PATENT DOCUMENTS

| CN | 105581779 A | 5/2016 |
| CN | 108814550 A | 11/2018 |
| WO | 2017223560 A1 | 12/2017 |

OTHER PUBLICATIONS

The International Search Report of corresponding International application No. PCT/CN2018/122661, dated Mar. 20, 2019.

\* cited by examiner

NEAR-INFRARED SPECTROSCOPY TOMOGRAPHY RECONSTRUCTION METHOD BASED ON NEURAL NETWORK

CROSS-REFERENCE TO RELATED APPLICATION

This application is a national phase application of international application No. PCT/CN2018/122661 filed on Dec. 21, 2018, which in turn claims the priority benefits of Chinese application No. 201810338705.2, filed on Apr. 16, 2018. The contents of these prior applications are hereby incorporated by reference in their entirety.

TECHNICAL FIELD

The present disclosure belongs to the field of medical image processing, especially to a near-infrared spectroscopy tomography reconstruction method based on neural network.

BACKGROUND ART

Near-infrared spectroscopy tomography is a new imaging technique and a non-destructive testing methods all over the world. The application of near-infrared light as an imaging source has attracted extensive attention. The technical principle is: substances such as blood sugar and oxygen vary in different tissues which lead to differences in the absorption coefficient of near infrared light$\mu_a$ and other optical parameters. Optical parameters, which are used to describe the optical properties of biological tissues, are also related to different physiological states of biological tissues. Based on these characteristics, the measurement of optical characteristics of organisms by near-infrared light can be used for imaging lesions or investigating the relative changes of biological optical parameters and other medical diagnostic items.

Compare with other method such as Computed Tomography, Magnetic Resonance Imaging, and Ultrasound Imaging, Near-infrared spectroscopy tomography has many significant advantages:

(1) Short imaging time, high time resolution, fast data acquisition speed.
(2) No ionizing radiation, no harm to the body, safe and reliable.
(3) Portable and easy to use, low cost, continuous disease monitoring.

Therefore, Near-infrared spectroscopy tomography has a wide range of uses and can be applied to various types of blood oxygen detection, such as brain functional imaging, breast cancer detection, neonatal brain detection, etc. It is also often used in small animal imaging directions.

Due to the boundary measurement data in the actual measurement process is limited and the inevitable mixed noise in measured near-infrared signal, the distribution of optical parameters with multiple finite element nodes should be reconstructed in the end which lead to the reconstruction of near-infrared spectral tomography becomes a discomfort and sickness problem in mathematics. Therefore, how to reconstruct the photoacoustic signal quickly and accurately is the key and difficult point in the study of near-infrared spectral tomography.

In order to solve the above problems, the regularization method is often used in reconstruction to transform the near-infrared image reconstruction problem into a nonlinear optimization problem. However, the ability of traditional methods to suppress artifacts in reconstructed images is weak and the imaging reconstruction time is relatively long. Therefore, the present disclosure considers using neural network to reconstruct near-infrared spectral images.

Artificial neural network (ANN), originated in the 1940s, is a hot topic in the field of artificial intelligence in recent years. It simulates the neural network of human brain, establish some simple model, form different networks according to different connection ways and complete various information processing tasks. BP neural network is the most widely used form of neural network. It was first discovered independently by David Runelhart, Geoffrey Hinton and Ronald w-llians, and David parker in the mid-1980s. It has good nonlinear mapping ability, self-learning ability, adaptive ability, generalization ability and fault-tolerant ability, so it is widely used in function approximation, pattern recognition, classified data compression and other aspects.

SUMMARY

The purpose of the present invention is to propose a near-infrared spectroscopy tomography reconstruction method based on neural network, which can improve the accuracy of the reconstructed image and reduce the imaging time. In order to realize the above purposes, the technical scheme adopted by the invention is:

1. In the Boltzmann radiation transmission equation, transmission process of light is regarded as absorption and scattering process of photons in medium, and interaction between light and tissue is determined by absorption coefficient, scattering coefficient and phase function of the response scattering distribution. In the transmission, only the particle property of light is taken into account, not the fluctuation of light. Therefore, polarization and interference phenomena related to the fluctuation of light are not considered, and only the energy transmission of light is tracked. energy diffusion approximation equation of light in tissue is expressed as:

$$\frac{1}{c}\frac{\partial \Phi(r,t)}{\partial t} + \mu_a \Phi(r,t) - \nabla \cdot \kappa(r)\nabla\Phi(r,t) = q_0(r,t) \tag{1}$$

wherein, c represents the speed at which light travels through the tissue, t represents time, r represents coordinate position vector, $\kappa$ represents scattering coefficient, $\mu_a$ represents absorption coefficient; $\Phi(r, t)$ represents photon fluence rate at position r; $q_0(r, t)$ represents light source; the diffusion approximation equation under continuous wave mode is adopted without considering the influence of time on diffusion equation:

$$-\nabla \cdot \kappa(r)\nabla\Phi(r) + \mu_a(r)\Phi(r) = q_0(r) \tag{2}$$

wherein $q_0(r)$ represents Isotropic light source; $\Phi(r)$ represents photon density distribution at position r;

In bioluminescence tomography, boundary conditions should also be considered in mathematical model. When refractive index of medium inside and outside the boundary is not same, the photon will reflect when it reaches boundary. the boundary condition corresponding to steady-state diffusion equation in near-infrared optical tomography is: air tissue boundary is expressed by exponential mismatch type III condition which is also known as Robin or mixed boundary condition which is expressed as:

$$\Phi(\xi) + 2A_n(\xi)\hat{n}\cdot\kappa(\xi)\nabla\Phi(\xi) = 0 \tag{3}$$

wherein ξ represents point on the outer boundary of tissue; n̂ represents the unit outer normal; $A_n$ depends on mismatched relative refractive index (RI) between tissue and air and is expressed as:

$$A_n = \frac{1+R_n}{1-R_n} \tag{4}$$

wherein $R_n$ represents internal reflection coefficient of diffusion transmission; n is related to optical refraction coefficient deviation inside and outside the boundary; based on the distribution of optical parameters, finite element method (FEM) and light approximate transmission equation is adopted to obtain boundary measured value Φ, Φ is used as the input of BP neural network x, then the output y of the network is the corresponding optical parameter distribution.

The structure of BP neural network is shown in FIG. 1.

2. The training of BP neural network is divided into two parts, forward propagation and back propagation; the first is the forward propagation process; set an input layer, a hidden layer and an output layer of BP network, wherein the input layer contain m nodes, the hidden layer contain q nodes and the output layer contain n nodes respectively; the weight between the input layer and the hidden layer is $v_{ki}$, and the weight between the hidden layer and the output layer is $w_{jk}$; activation functions from the input layer to the hidden layer and from the hidden layer to the output layer are respectively expressed as $f_1(\cdot)$ and $f_2(\cdot)$; the output of hidden layer node $z_k$ is:

$$z_k = f_1\left(\sum_{i=1}^{m} v_{ki} x_i\right) k = 1, 2, \ldots, q \tag{5}$$

the output of output layer node $y_i$ is:

$$y_i = f_2\left(\sum_{k=1}^{q} w_{jk} z_k\right) j = 1, 2, \ldots, n \tag{6}$$

the second part is back propagation; firstly, set the mean square error function (MSE) as a loss function; the overall mean square error of m samples can be expressed as:

$$E = \frac{1}{2}\sum_{i=1}^{m}\sum_{j=1}^{n}(Y_j^i - y_j^i)^2 = \sum_{i=1}^{m} E_i \tag{7}$$

the overall error is reduced by using steepest descent method, and the change of weight is expressed as:

$$\Delta w_{jk} = -\eta \frac{\partial E}{\partial w_{jk}} = -\eta \frac{\partial}{\partial w_{jk}}\left(\sum_{i=1}^{m} E_i\right) = \sum_{i=1}^{m} -\eta \frac{\partial E_i}{\partial w_{jk}} \tag{8}$$

wherein, η represents learning rate; set the error signal as:

$$\delta_{yj} = -\frac{\partial E_i}{\partial S_j} = -\frac{\partial E_i}{\partial y_j}\cdot\frac{\partial y_j}{\partial S_j} = \sum_{j=1}^{n}(Y_j^i - y_j^i)f_2'(S_j) \tag{9}$$

wherein $S_j = \sum_{k=1}^{q} w_{jk} z_k$, according to the chain theorem, weight adjustment formula of the output layer is:

$$\Delta w_{jk} = \sum_{i=1}^{m}\sum_{j=1}^{n} \eta(Y_j^i - y_j^i)f_2'(S_j)z_k \tag{10}$$

similarly, the weight adjustment formula of each node in the hidden layer is:

$$\Delta v_{ki} = \sum_{i=1}^{m}\sum_{j=1}^{n} \eta(Y_j^i - y_j^i)f_2'(S_j)w_{jk}f_1'(S_k)x_i \tag{11}$$

BP neural network updates weight and bias with above formula (5)-(11) until the error meets the requirements or other stopping conditions. The network output is optical absorption coefficient distribution.

PREFERRED EMBODIMENT

The invention is described in detail accompanied with the appended drawings.

Figure 1:
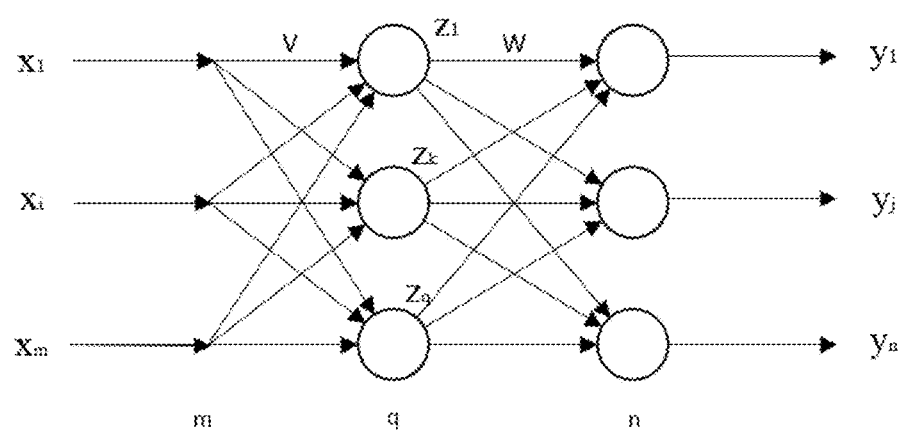
FIG. 1 is schematic diagram of BP neural network, wherein "x" is input and the dimension is "m", "y" is output and the dimension is "n", "z" is output of hidden layer and the dimension is "q". are "v" and "w" are weights of input layer to hidden layer and hidden layer to output layer respectively.
Figure 2:
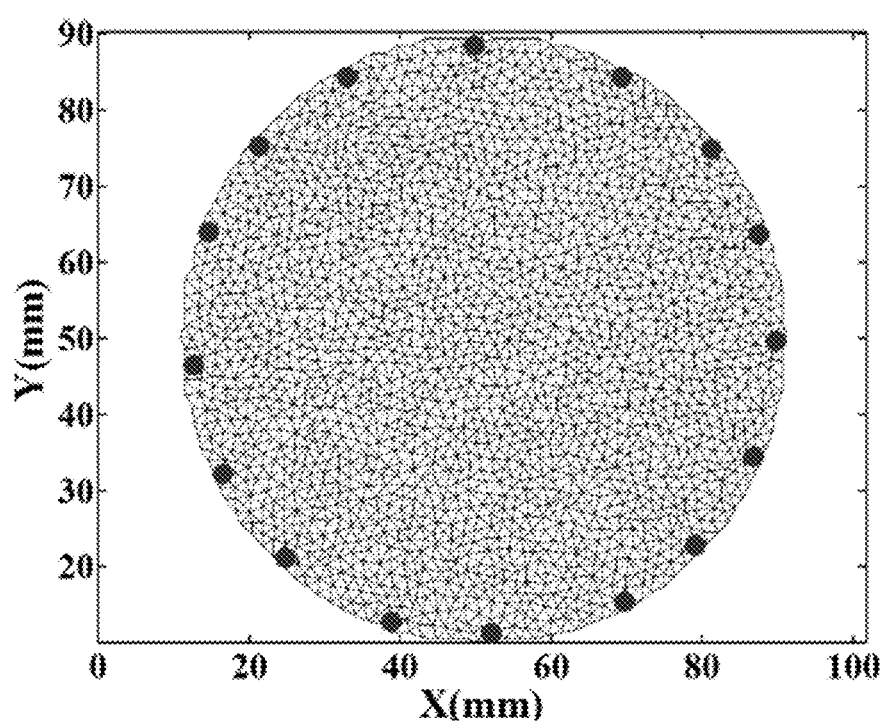
FIG. 2 is finite element mesh of replica, has a total of 2001 nodes.
Figure 3:
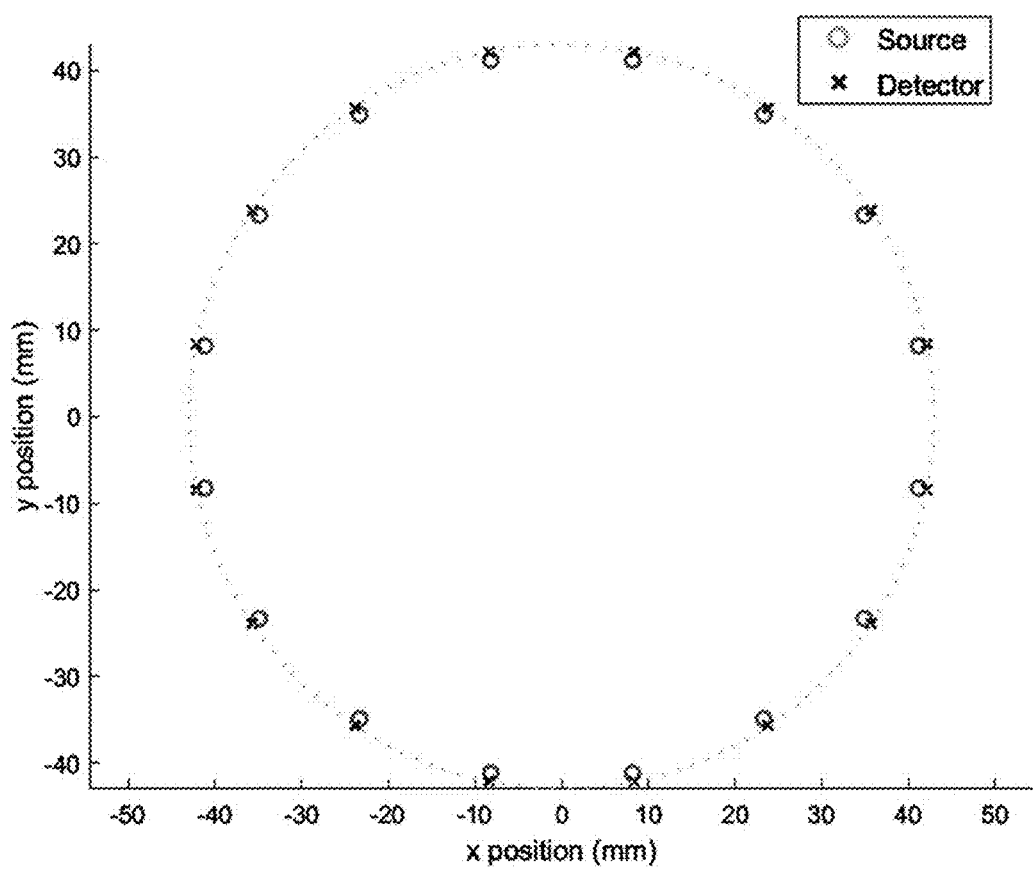
FIG. 3 shows the position of light source and detector.
Figure 4:
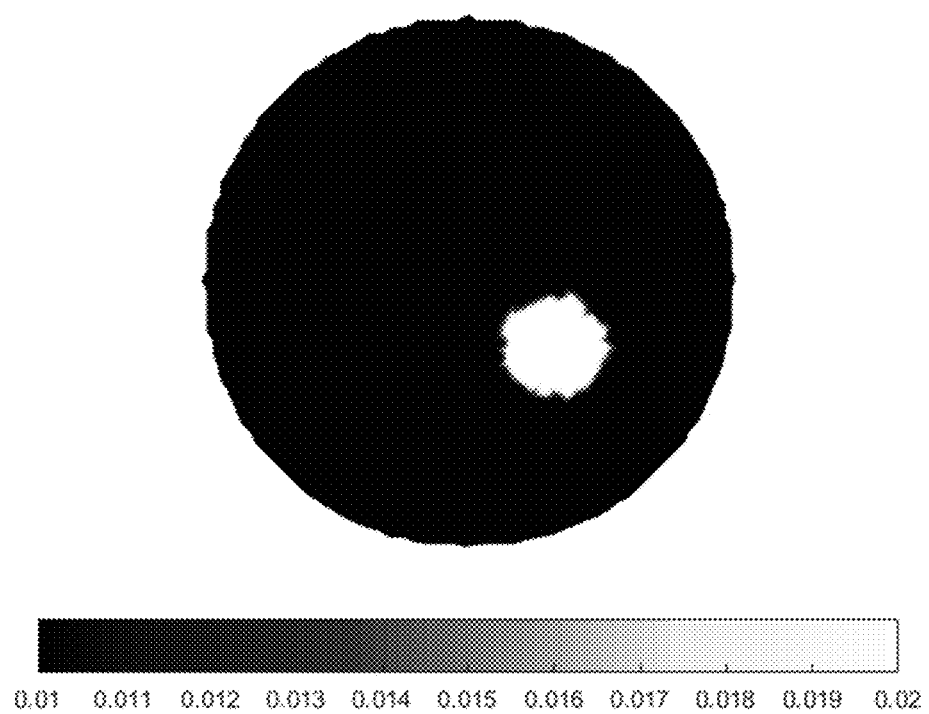
FIG. 4 shows the initial absorption coefficient distribution of the replica, the large black circular area is the background area, and absorption coefficient is set as 0.01, the smaller white area in black area is abnormal area added in background, and its absorption coefficient is set as 0.02.

First, establish replica and finish the finite element mesh generation through Matlab toolbox nirfast, circular replica is used, and the finite element mesh generation results is shown in FIG. 2. A total of 16 light sources and 16 light detectors are set up in the experiment. These detectors are placed on outer boundary of a circular replica with a diameter of 80 mm as shown in FIG. 3, 256 measurements can be obtained through the light source and detector, and the imaging pixels are 2001 uniform finite element nodes on the circle. The measured value and absorption coefficient of each finite element node are taken as the input and output of BP neural network. Initial absorption coefficient distribution is shown in FIG. 4. The data set used for network training is calculated through forward solving process of nirfast toolbox's. There are 1027 samples in data set, including 927 samples in training set and 100 samples in test set, each sample contains an abnormal region. Each abnormal region is a circular region with a radius of √60, and the center position of each sample abnormal region is different.

The reconstruction method based on BP neural network is used to reconstruct the distribution of optical absorption coefficient, In the experiment, set the number of iterations epoch=20000, learning rate η=1, node number of hidden layers q=100, anticipation error is $1\times10^{-5}$, weight and the bias are set between (−1,1). Experimental results show that the above parameters can be used to obtain a better reconstruction effect.

Figure 5:
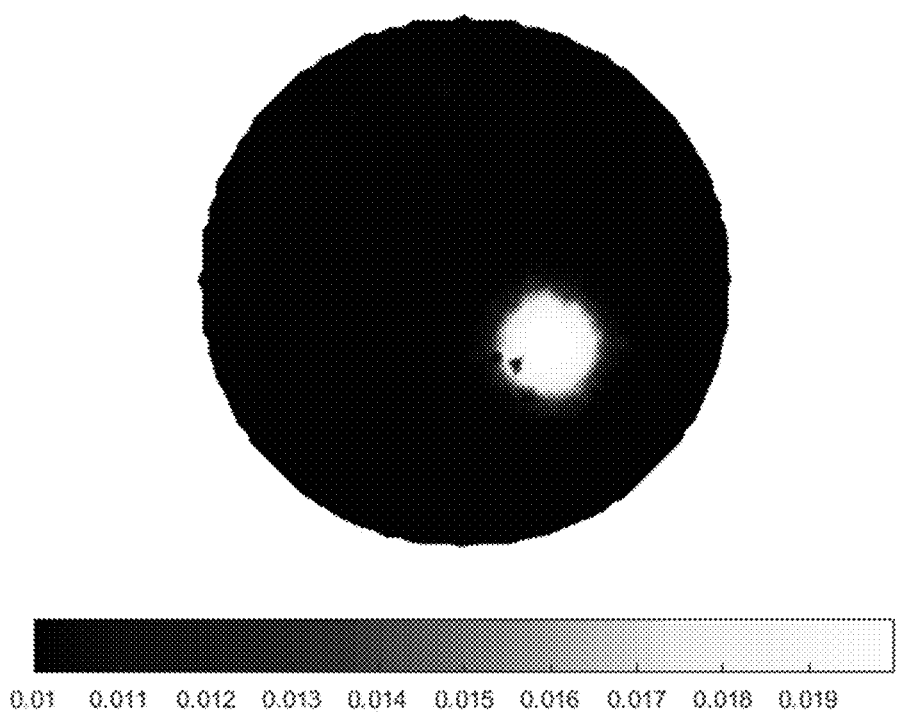
FIG. 5 is the results of absorption coefficient distribution reconstructed by this method.

The invention uses a reconstruction method of optical absorption coefficient distribution based on BP neural network. Reconstruction result of absorption coefficient distribution as shown in FIG. 5 can be obtained by this method, the training time is 54 minutes and reconstruction time is 0.066849s. Experimental results show that this method can not only reconstruct the absorption coefficient distribution accurately, but also has high computational efficiency.

What is claimed is:

1. A near-infrared spectroscopy tomography reconstruction method based on neural network applied to biological tissue, comprising: an energy diffusion approximation equation (1) of light in the biological tissue is expressed as:

$$\frac{1}{c}\frac{\partial \Phi(r, t)}{\partial t} + \mu_a\Phi(r, t) - \nabla \cdot \kappa(r)\nabla\Phi(r, t) = q_0(r, t) \quad (1)$$

wherein, c represents a speed at which light travels through the tissue, t represents time, r represents a coordinate position vector, κ represents scattering coefficient, $\mu_a$ represents absorption coefficient; Φ(r, t) represents a photon fluence rate at position r; $q_0(r,t)$ represents a light source; an energy diffusion approximation equation (2) under continuous wave mode is adopted without considering an influence of time on the energy diffusion approximation equation (1):

$$-\nabla \cdot \kappa(r)\nabla\Phi(r) + \mu_a(r)\Phi(r) = q_0(r) \quad (2)$$

wherein $q_0(r)$ represents an isotropic light source; Φ(r) represents photon density distribution at position r;

a boundary condition corresponding to steady-state diffusion equation in near-infrared optical tomography is: air tissue boundary is expressed by exponential mismatch type III condition which is also known as Robin or mixed boundary condition which is expressed as:

$$\Phi(\xi) + 2A_n(\xi)\hat{n} \cdot \kappa(\xi)\nabla\Phi(\xi) = 0 \quad (3)$$

wherein ξ represents point on an outer boundary of tissue; $\hat{n}$ represents a unit outer normal; $A_n$ depends on mismatched relative refractive index (RI) between tissue and air and is expressed as:

$$A_n = \frac{1+R_n}{1-R_n} \quad (4)$$

wherein $R_n$ represents internal reflection coefficient of diffusion transmission; n is related to optical refraction coefficient deviation inside and outside the outer boundary;

based on a distribution of optical parameters, finite element method (FEM) and light approximate transmission equation is adopted to obtain outer boundary measured value Φ, Φ is used as an input of back propagation (BP) neural network x, then an output y of the BP neural network is a corresponding optical parameter distribution;

the near-infrared spectroscopy tomography reconstruction method further comprises:

establishing circular replica and finishing finite element mesh generation through Matlab toolbox nirfast; wherein a plurality of light sources and light detectors are set up along an outer boundary of the circular replica, measurements are obtained through the light sources and the light detectors, and imaging pixels are uniform finite element nodes on the circular replica; measured value and absorption coefficient of each finite element node are taken as the input and the output of the BP neural network, respectively;

data set used for training of the BP neural network is calculated through forward solving process of nirfast toolbox's; there are a plurality of samples in the data set, including samples in a training set and samples in a test set, each sample contains an abnormal region, the abnormal region is a circular region with a radius, and a center position of the abnormal region for different sample is different.

2. The near-infrared spectroscopy tomography reconstruction method based on neural network applied to biological tissue according to claim 1, a training of the BP neural network is divided into two parts, forward propagation and back propagation; the first part is the forward propagation; set an input layer, a hidden layer and an output layer of the BP neural network, wherein the input layer contains m nodes, the hidden layer contains q nodes and the output layer contains n nodes respectively; a weight between the input layer and the hidden layer is $v_{ki}$, and a weight between the hidden layer and the output layer is $w_{jk}$; activation functions from the input layer to the hidden layer and from the hidden layer to the output layer are respectively expressed as $f_1(\bullet)$ and $f_2(\bullet)$; an output of hidden layer node $z_k$ is:

$$z_k = f_1\left(\sum_{i=1}^{m} v_{ki}x_i\right) k = 1, 2, \ldots, q \quad (5)$$

an output of output layer node $y_i$ is:

$$y_i = f_2\left(\sum_{k=1}^{q} w_{jk}z_k\right) j = 1, 2, \ldots, n \quad (6)$$

the second part is the back propagation; firstly, set mean square error function (MSE) as a loss function; the MSE of m samples is expressed as:

$$E = \frac{1}{2}\sum_{i=1}^{m}\sum_{j=1}^{n}(Y_j^i - y_j^i)^2 = \sum_{i=1}^{m} E_i \quad (7)$$

the MSE is reduced by using steepest descent method, and a change in each of the weights is expressed as:

$$\Delta w_{jk} = -\eta \frac{\partial E}{\partial w_{jk}} = -\eta \frac{\partial}{\partial w_{jk}}\left(\sum_{i=1}^{m} E_i\right) = \sum_{i=1}^{m} -\eta \frac{\partial E_i}{\partial w_{jk}} \quad (8)$$

wherein, $\eta$ represents learning rate;
set an error signal as:

$$\delta_{yj} = -\frac{\partial E_i}{\partial S_j} = -\frac{\partial E_i}{\partial y_j} \cdot \frac{\partial y_j}{\partial S_j} = \sum_{j=1}^{n}(Y_j^i - y_j^i)f_2'(S_j) \quad (9)$$

wherein $S_j = \Sigma_{k=1}^{q} w_{jk} z_k$, according to the chain theorem, weight adjustment formula of the output layer is:

$$\Delta w_{jk} = \sum_{i=1}^{m}\sum_{j=1}^{n} \eta(Y_j^i - y_j^i)f_2'(S_j)z_k \quad (10)$$

weight adjustment formula of each node in the hidden layer is:

$$\Delta v_{ki} = \sum_{i=1}^{m}\sum_{j=1}^{n} \eta(Y_j^i - y_j^i)f_2'(S_j)w_{jk}f_1'(S_k)x_i \quad (11)$$

the BP neural network updates weight and bias with above formula (5)-(11) until the MSE meets a predetermined requirement, an output of the BP neural network is optical absorption coefficient distribution.

* * * * *